(12) United States Patent
Schulz et al.

(10) Patent No.: US 11,401,300 B2
(45) Date of Patent: Aug. 2, 2022

(54) PROCESS FOR PRODUCTION OF FIBRINOGEN AND FIBRINOGEN PRODUCED THEREBY

(71) Applicant: OCTAPHARMA AG, Lachen (CH)

(72) Inventors: Petra Schulz, Vienna (AT); Werner Gehringer, Vienna (AT); Friedrich Schön, Vienna (AT); Caroline Leitinger, Vienna (AT); Jürgen Römisch, Vienna (AT); Rainer Pape, Vienna (AT)

(73) Assignee: OCTAPHARMA AG, Lachen (CH)

( * ) Notice: Subject to any disclaimer, the term of this patent is extended or adjusted under 35 U.S.C. 154(b) by 0 days.

(21) Appl. No.: 16/136,003

(22) Filed: Sep. 19, 2018

(65) Prior Publication Data

US 2019/0016755 A1   Jan. 17, 2019

Related U.S. Application Data

(62) Division of application No. 14/382,712, filed as application No. PCT/EP2013/054983 on Mar. 12, 2013, now Pat. No. 10,112,972.

(60) Provisional application No. 61/610,030, filed on Mar. 13, 2012.

(30) Foreign Application Priority Data

Mar. 12, 2012 (EP) .................... 12159276

(51) Int. Cl.
*C07K 1/36* (2006.01)
*C07K 14/75* (2006.01)

(52) U.S. Cl.
CPC ............... *C07K 1/36* (2013.01); *C07K 14/75* (2013.01)

(58) Field of Classification Search
None
See application file for complete search history.

(56) References Cited

U.S. PATENT DOCUMENTS

| | | | |
|---|---|---|---|
| 4,116,635 A | 9/1978 | Jaeger | |
| 4,650,678 A | 3/1987 | Fuhge et al. | |
| 4,960,757 A | 10/1990 | Kumpe et al. | |
| 5,330,974 A * | 7/1994 | Pines | A61L 24/106 514/13.6 |
| 5,834,420 A * | 11/1998 | Laub | A61L 2/0088 514/14.3 |
| 6,037,457 A | 3/2000 | Lord | |
| 6,447,774 B1 | 9/2002 | Metzner et al. | |
| 6,468,733 B2 | 10/2002 | Nur et al. | |
| 7,009,039 B2 | 3/2006 | Yayon et al. | |
| 7,045,601 B2 | 5/2006 | Metzner et al. | |
| 7,211,650 B2 | 5/2007 | McCreath et al. | |
| 7,442,308 B2 | 10/2008 | Ristol Debart et al. | |
| 7,550,567 B2 | 6/2009 | Metzner et al. | |
| 7,919,592 B2 | 4/2011 | Lengsfeld et al. | |
| 2003/0138913 A1 | 7/2003 | Josic et al. | |
| 2006/0009376 A1 | 1/2006 | Eibl | |
| 2008/0003272 A1 | 1/2008 | Rapp et al. | |
| 2008/0171878 A1 | 7/2008 | Schils et al. | |
| 2008/0181878 A1 | 7/2008 | Farrell | |
| 2008/0207878 A1 | 8/2008 | Michel et al. | |
| 2011/0114524 A1 | 5/2011 | Eibl | |
| 2013/0274444 A1 * | 10/2013 | Schulz | C07K 14/75 530/382 |

FOREIGN PATENT DOCUMENTS

| | | |
|---|---|---|
| CN | 1425024 A | 6/2003 |
| CN | 101703763 A | 5/2010 |
| EP | 0 131 740 A2 | 1/1985 |
| EP | 0 555 135 A1 | 8/1993 |
| EP | 0 771 324 A1 | 5/1997 |
| EP | 1 240 200 A1 | 9/2002 |
| EP | 1250929 A1 | 10/2002 |
| EP | 1393741 A1 | 3/2004 |
| EP | 1519944 A1 | 4/2005 |
| EP | 1739093 A1 | 1/2007 |
| EP | 1457497 B1 | 10/2008 |
| EP | 1519944 B1 | 11/2009 |
| EP | 2928905 A1 | 10/2015 |
| FK | 0555135 A1 | 8/1993 |
| WO | 95/022316 A1 | 8/1995 |
| WO | 96/02571 A1 | 2/1996 |
| WO | 1996/002571 A1 | 2/1996 |
| WO | 2000047621 A1 | 8/2000 |
| WO | 01/48016 A1 | 7/2001 |
| WO | 2004007533 A1 | 1/2004 |
| WO | 2009/155626 A2 | 12/2009 |

(Continued)

OTHER PUBLICATIONS

RiaSTAP™ Fibrinogen Concentrate (Human) CSL Behring product sheets, 2009: 11 pages. (Year: 2009).*
Okuda, M., et al. 2003 Clin Lab Haem 25: 167-172. (Year: 2003).*
Burnouf-Radosevich et al., "Biochemical and Physical Properties of a Solvent-Detergent-Treated Fibrin Glue" Vox Sang 1990, 58:77-84.
Chinese Office Action (with English translation) dated May 6, 2014, issued in Chinese Application No. 201180045268.1.
Fernandez, et al., "Structural and Functional Analysis of the Complex between Citrate and the Zinc Peptidase Carboxypeptidase A," SAGE—Hindawi Access to Research Enzyme Research, (2011) 1-8.

(Continued)

*Primary Examiner* — Marsha Tsay
(74) *Attorney, Agent, or Firm* — Venable LLP; Keith G. Haddaway; Daniel M. Podgorski

(57) ABSTRACT

A process for purifying fibrinogen from a fibrinogen containing source by precipitation of fibrinogen by a precipitating agent from a fibrinogen containing solution in the presence of one or more chelating agent(s) and removal of the supernatant from the fibrinogen paste, characterised in that fibrinogen is extracted from the paste forming a liquid fraction containing fibrinogen, and an undissolved residue, which is separated from the liquid.

7 Claims, 1 Drawing Sheet

(56) References Cited

FOREIGN PATENT DOCUMENTS

| WO | 2012038410 A1 | 3/2012 |
| WO | 2013135684 A1 | 9/2013 |
| WO | 2014085861 A1 | 6/2014 |

OTHER PUBLICATIONS

GE Health Care "Ion Exchange Chromatography & Chromatofocusing Principles and Methods" 2010.

Glusker, "Citrate Conformation and Chelation: Enzymatic Implications," Acc. Chem. Res. 1980, 13, 345-352.

Goheen S. C. et al: "High-performance ion-exchange chromatography and adsorption of plasma proteins", Journal of Chromatography, Elsevier Science Publishers B.V., NL, vol. 816, No. 1, Aug. 7, 1998, pp. 89-96.

Holm et al., "Purification and Characterization of 3 Fibrinogens with Different Molecular Weights Obtained from Normal Human Plasma," Thrombosis Research, 37 (1985) 165-176.

International Preliminary Report on Patentability issued in PCT Application No. PCT/EP2013/054983 dated Sep. 16, 2014.

International Preliminary Report on Patentability issued in PCT International Application No. PCT/EP2011/066293 dated Mar. 26, 2013.

International Search Report and Written Opinion issued in PCT International Application No. PCT/EP2011/066293 dated Dec. 23, 2011.

International Search Report dated May 23, 2013, issued in INternational Application No. PCT/EP2013/054983.

Jung et al., "The Vroman Effect: A Molecular Level Description of Fibrinogen Displacement," J. Am. Chem. Soc., 125.42, (2003) 12782-12786.

Kazal, et al., "The Preparation and Some Properties of Fibrinogen Precipitated from Human Plasma by Glycine," P.S. E.B.M., v113 (1963) 989-994.

Lottspeich F., et al., "Auflage; Spektrum Akade-mischer Verlag," (2006) 19.

Okuda et al., "Quality control material for plasma fibrinogen test produced from purified human fibrinogen," J. of Automated Methods & Management in Chem., 25.4, (2003) 79-85.

Opposition of application EP2825555, dated Apr. 12, 2018.

Opposition of application EP2825555, dated Apr. 9, 2018.

Pohl et al., "Effects of the deletion of the *Escherichia coil* frataxin homologue CyaY on the respirator NADH:ubiquinone oxidoreductase" BMC Biochemistry 2007, 8:13 1-10.

Sigma Aldrich "Analytical Enzymes Fibrinogen and Fibrin" 2004.

Third party submission under 37 CFR 1.290 filed on Aug. 7, 2015 for U.S. Appl. No. 14/382,712, filed Feb. 12, 2015 (14 pages).

Tosoh Bioscience "Toyopearl GigaCap Q-650M for high capacity Anion Exchange Chromatography of small and large proteins," 2008.

Becker et al., "Bovine Fibrinogen Aggregates: Electron Microscopic Observations of Quasi-Globular Structures", Thrombosis Research 48; 101-110, 1987.

Gollwitzer et al., "On the Aggregation of Fibrinogen Molecules", Thrombosis Research, Supplement V; 41-53, 1983.

U.S. Appl. No. 61/733,761, filed Dec. 5, 2012.

Experimental Report from Opposition in EP2825555 (dated Apr. 9, 2018).

Response filed in corresponding EP2825555 (dated Mar. 24, 2016).

Wikipedia extract submitted in Opposition in EP2825555 (from Feb. 4, 2011).

Search Report for priority document in PCT/EP2013/054983 (EP 12159276.0) dated Jun. 20, 2012.

Priority document for WO2014/085861 (EP 13153898.5) filed Feb. 4, 2013 (publicly available Jun. 12, 2014).

Marx (J Biomed Mater Res Part B: Appl Miomater, 2008, 84B, 1, 49-57; abstract only).

Roizenblatt et al., "7S IgG rheumatoid factor and hidden 19S IgM rheumatoid factor in juvenile chronic arthritis", Allergol Immunopathol (Madr)., (Sep.-Oct. 1993), vol. 21, No. 5, pp. 197-200 (abstract only).

Ross, "The Kinetics of the Thrombin Catalyzed Fibrinogen Fibrin Conversion", (Jun. 1965), Master's Theses, 1998, https://ecommons.luc.edu/luc_theses/1998.

Schwartz et al., "Global Development Plan for a Double Virus Inactivated Fibrinogen Concentrate for the Treatment of Congenital Fibrinogen Deficiency", Clinical Issue and Trials, 2014.

\* cited by examiner

PROCESS FOR PRODUCTION OF FIBRINOGEN AND FIBRINOGEN PRODUCED THEREBY

CROSS-REFERENCE TO RELATED APPLICATIONS

This application is a Divisional of U.S. patent application Ser. No. 14/382,712, filed Sep. 3, 2014, which is a U.S. National Stage of International Application No. PCT/EP2013054983, filed Mar. 12, 2013, which claims priority to U.S. Provisional Application No. 61/610,030, filed Mar. 13, 2012, and European Application No. 12159276.0 filed Mar. 13, 2012, the entire contents of each of which are hereby incorporated by reference.

DESCRIPTION

The present invention relates to a process for purifying fibrinogen from a fibrinogen containing source, a fibrinogen product obtainable according to the process of the invention as well as an anion exchange resin selected from the group consisting of a support material comprising a hydroxylated polymer backbone with grafted tertiary or quaternary amino groups for purification or manufacturing of a fibrinogen product.

BACKGROUND OF THE INVENTION

Fibrinogen, also known as clotting factor I, plays a key role in haemostasis and wound healing. It is a glycoprotein synthesized in the liver with an apparent molecular weight of 340,000 Da, is composed of two dimers, each of them built of three pairs of non-identical polypeptide chains called A$\alpha$, B$\beta$ and $\gamma$ linked by disulfide bridges. It circulates in the blood stream at a concentration of approximately 1.5-4.0 mg/ml. Upon injury of blood vessels, blood platelets are activated and a plug is formed. Fibrinogen is involved in primary haemostasis by aiding cross-linking of activated platelets.

In parallel activation of the clotting cascade is initiated. As the endpoint, fibrinogen is converted into fibrin by proteolytic release of fibrinopeptide A and—at a slower rate—fibrinopeptide B by thrombin. The soluble fibrin monomers are assembled to double stranded twisted fibrils. Subsequently these fibrils are arranged in a lateral manner, resulting in thicker fibers. These fibers are then cross-linked by FXIIIa to a fibrin network, which stabilizes the platelet plug by interactions of the fibrin with activated platelets, resulting in a stable clot.

Disorders and Deficiencies

Congenital afibrinogenaemia is a rare bleeding disorder, where patients are suffering from inadequate clotting of the blood due to lacking or malfunction of fibrinogen. This medical condition might lead to spontaneous bleeding episodes or excessive bleeding after minor traumata or during interventional procedures.

Acquired deficiencies in fibrinogen are much more common than congenital afibrinogenaemia and may be induced by haemodilution or other events such as blood losses during surgery, traumata, disseminated intravascular coagulation (DIC) or sepsis.

Fibrinogen deficiencies can be corrected to normal fibrinogen levels in plasma of about 1.5-4 g/l by replacement therapy with intravenous infusion of fresh frozen plasma or cryoprecipitate. However, these treatments are afflicted with the risk of introduction of pathogens, e.g. viruses or prions, into a patient and are thereby generating additional disorders. It is thus advisable to intravenously apply virus inactivated fibrinogen compositions to restore fibrinogen at physiological levels in a save way.

While there exists fibrinogen in preparations called fibrin glue, fibrinogen adhesive, tissue glue and similar, these preparations are intended for topical use as powders, pastes, foams or in combination with fabrics as plaster on wounds, they are not usable for intravenous application as their consistency and composition would immediately initiate thrombotic events when being injected. These preparations additionally contain thrombin, calcium salts and relatively high amounts of coagulation factor XIII. Examples for such preparations are US-A1-2008/003272, WO-A-95/22316 or US-A1-2008/181878.

Processes for fibrinogen production are known from EP-A1-1 240 200 which relates to a method of purifying fibrinogen from a fibrinogen containing solution, comprising, application of a fibrinogen containing solution to an ion exchange matrix, under conditions such that fibrinogen binds to the matrix, washing the ion exchange matrix with a buffer solution comprising at least one $\omega$-amino acid, eluting the fibrinogen from the matrix with a buffer consisting of 10 mM Tris, 10 mM citrate, 45 mM sucrose and NaCl at a concentration of 200 mM to 1.0 M, and optionally recovering the fibrinogen from the eluate.

EP-A1-0 771 324 refers to a process for production of a virus free fibrinogen concentrate which is obtained by subjecting a solubilised plasma fraction containing fibrinogen to a chemical viral inactivation treatment, i.e. a S/D or solvent/detergent treatment, subjecting the resulting viral-inactivated fraction to precipitation in a solution containing an amino acid at an acidic pH to obtain a supernatant, filtering the supernatant to obtain a purified fibrinogen concentrate, and recovering the purified fibrinogen concentrate. The recovered fibrinogen concentrate is subjected to ultra violet radiation for a second virus inactivation. The product is stabilized and lyophilized prior to a third virus inactivation step.

EP-A1-1 519 944 teaches the use of an immobilized metal ion affinity chromatography matrix under conditions that the fibrinogen and plasminogen bind to the matrix, and selectively eluting the fibrinogen and 93% of plasminogen separately from the matrix.

EP-A1-0 555 135 discloses a method for production of an intravenously applicable fibrinogen by purification of a fibrinogen solution by means of an anion exchange gel based on cross-linked agarose comprising quaternary amine groups. The fibrinogen produced is said to be free of factor VIIIc.

EP-A1-1 457 497 refers to a process for removing viruses in fibrinogen solutions characterized by stabilization and freezing of the solution and subsequent thawing thereof. Separation of undissolved materials occurs prior to dilution of the protein and is followed by nanofiltration of the resultant solution using filters of a pore size smaller than 35 nm.

US-A1-2006/0009376 also discloses a method to manufacture fibrinogen, following repeated dissolution and precipitation of fibrinogen to remove factor XIII.

WO-A2-2009/155626 refers to a process for purification of fibrinogen by solubilisation of cryoprecipitate or Cohn-Fraction I in an EDTA-solution at a temperature range of 3° C. to 5° C., followed by fractionated precipitation in a temperature range of 2° C. to 4° C. and dissolution of the last precipitate in an EDTA-solution. Virus inactivation with S/D reagents and nanofiltration for improvement of pathogen safety occur in the presence of EDTA. Inhibition of residual amounts of proteases in the produced concentrate is accomplished by addition of AT-III, heparin-cofactor-II and C1-esterase-inhibitor.

U.S. Pat. No. 7,919,592 B2 describes a method for removing viruses from fibrinogen solutions by addition of chaotropic substances, chosen from arginine, guanidine, citrulline and urea, there salts or derivatives and subsequent filtration through nanofilters of various pore size.

Goheen, S. C. et al. report in Journal of Chromatography A. 816 (1998) 89-96, about HPLC ion-exchange chromatography of the plasma proteins albumin, fibrinogen, and immunoglobulin (G) on nonporous column materials containing either quaternary amine or sulfopropyl functional groups.

SUMMARY OF THE INVENTION

One object of the invention is providing of a fibrinogen concentrate manufactured with dedicated pathogen eliminating and/or inactivation steps in the production process in order to overcome adverse reactions or development of pathogen related illnesses. Said pathogens are selected from the groups of bacteria, viruses and prions, such as prion protein scrapie ($PrP^{sc}$).

Nanofiltration is a method in principle known to remove viruses from proteins passing through the nanofilter, but separation of viruses from fibrinogen by nanofiltration is challenging as fibrinogen is a quite large and sticky protein frequently resulting in plugging of filter pores and eventual loss of product. One approach to overcome this problem is to add chaotropic substances to improve filterability as it is taught by U.S. Pat. No. 7,919,592B-2, although nanofiltration of a diluted fibrinogen solution produced according to the process of International Application WO-A1-2012/038410 revealed comparable filterability without addition of chaotropic substances. Chaotropic substances according to the invention are those as defined in U.S. Pat. No. 7,919,592 B2 incorporated by reference and designating arginine, guanidine, citrulline and urea, their salts or derivatives.

A further object of this application is providing of a process to manufacture a concentrate on an industrial level, i.e. several hundreds to thousands of liters starting material, such as blood or blood plasma, although a small scale production, i.e. some ⅒ liter to some liters, is also possible.

These and further objects are accomplished by a process of claims 1 to 18, a product as claimed in claims 19 to 24 obtainable by the process of the invention and the use of claim 25.

FIG. 1 depicts a SDS-Page at non-reducing conditions while FIG. 2 depicts a SDS-Page at reducing conditions of the same samples.

According to the present invention it has surprisingly been observed that precipitation of an intermediate fibrinogen paste in the presence of one or more chelating substances followed by extraction of fibrinogen from the intermediate provided a fibrinogen solution of better filterability than those produced by the process of WO-A1-2012/038410.

It was further surprisingly observed, that a one-time addition of a rather small amount of at least one chelating agent prior to precipitation, resulting in a total chelating agent concentration of about 3-10 mM, is sufficient for the present invention to provide both excellent yield and filterability, even with nanofilters providing retention of particles of <35 nm. Residual amounts of chelating agent can be removed downstream providing a final product, i.e. a fibrinogen concentrate which is free of chelating agent within the detection limit, which is lower than 0.08 μg/ml for EDTA. A product free of chelating agents is preferable as, for instance, EDTA is a known anti-coagulant. Thus the presence of EDTA in substantial amounts is counterproductive to the effects of a fibrinogen product.

Consequently, all buffers used downstream of the precipitation, e.g. equilibration-, washing- and elution-buffers used for chromatography or the buffer used during concentration by ultra-/diafiltration, should be free of $Ca^{2+}$-chelating agents, which are defined below. Residual amounts of eventually present chelating agents are removable from a fibrinogen containing solution by ultra-/diafiltration. This removal is advantageously performed by ultra-/diafiltration at the end of the process in particular during concentrating or formulating, if it should be necessary. Systemic application of such a fibrinogen product free of chelating agents via intravenous route allows treatment of congenital afibrinogenaemia and acquired fibrinogen deficiencies. Application of this standardized fibrinogen concentrate allows fast treatment in emergency situations without time-consuming thawing of fresh frozen plasma and lowered volume load and reliable coagulation properties due to essentially constant composition. Increased concentrations of coagulation factor XIII, compared to products disclosed in WO-A1-2012/038410 also support topical administration on wounds or the use as tissue glue.

It was further surprisingly observed, that an addition of protease inhibitors at any step of the process of the invention was unnecessary when the intermediate fibrinogen paste was precipitated in the presence of one or more chelating substances. The use of protease inhibitors such as C1-protease inhibitors, trypsin inhibitors, thrombin inhibitors, antithrombin-III (AT-III), heparin-cofactor-II, aprotinin, pepstatin, leupeptin and in particular epsilon-aminocaproic acid (ε-ACA) to avoid degradation of fibrinogen is known from prior art literature. The fibrinogen concentrate of the present invention displayed neither a measurable proteolytic activity nor a measurable AT-III concentration.

In general, the process of the invention for purification or manufacturing of fibrinogen from fibrinogen containing sources comprises the steps of:

forming a fibrinogen enriched precipitate by adding a chelating agent prior to addition of at least one precipitating agent to the fibrinogen containing source;

isolating the fibrinogen enriched precipitate e.g. by centrifugation of said precipitate;

extraction of fibrinogen from the fibrinogen enriched precipitate in an aqueous medium void of the chelating agent and thereby forming a fibrinogen containing solution, optionally followed by filtration and/or ultra/diafiltration;

subjecting the fibrinogen containing solution to a chromatography on a stationary phase having strong anion exchanger groups by contacting said solution with said phase under conditions that fibrinogen binds to said phase;

followed by an elution of fibrinogen from the stationary phase by means of an aqueous solution having a higher ionic strength than the ionic strength of the foregoing step, yielding a fibrinogen enriched fraction which is collected;

optionally followed by subsequent steps of dilution and/or concentration of the fibrinogen enriched fraction;

and optionally filling of the fibrinogen enriched fraction into suitable vials, while addition of protease inhibitors is omitted.

In one embodiment of the manufacturing process of the invention the fibrinogen containing source is selected from the group consisting of, blood plasma, plasma fractions, such as fraction I, or cryoprecipitate, cell cultures producing fibrinogen and/or supernatants of said cell cultures. If cryoprecipitate is not used as starting material, a fibrinogen containing intermediate as starting material is produced by well known methods like disclosed by Cohn, Kistler-Nitschmann and modifications thereof.

For obtaining a pharmaceutical usable product it is advantageous that the fibrinogen containing source is subjected to at least one virus inactivating process for example a solvent detergent process as disclosed in EP-A1-0 131 740 incorporated by reference.

According to another embodiment of the invention the virus inactivation is performed prior to forming a fibrinogen enriched precipitate. However, it is also possible to perform a virus inactivation at a different stage.

According to yet another embodiment of the invention the removal of virus inactivating substances is performed by oil extraction and/or chromatography with strong anion exchangers. Another method for virus removal is nanofiltration, due to the low content of polymers after fibrinogen extraction nanofiltration can be performed also well with filters<35 nm without addition of chaotropic substances.

A typical precipitating agent for use in the manufacturing process of the invention is selected from the group consisting of amino acids such as glycine, polyethylene glycol or high salt concentrations, wherein the salt contains monovalent metal ions, in particular selected from the group of alkali metals, or ammonium.

According to still another embodiment of the invention the extraction of fibrinogen from the fibrinogen enriched precipitate is performed with a buffer having a pH of 7.5 to 8.5 for 10 to 120 minutes.

According to a further embodiment of the invention the stationary phase has tertiary or quaternary amino groups.

The chromatography steps in the manufacturing process of the invention can in particular be performed in a column.

Typically the storage form of the filled fibrinogen enriched fraction is in liquid state, frozen state, preferably at <−15° C., most preferably below −30° C., or as lyophilisate.

The process of the invention comprises in detail the steps of
a) solubilisation of cryoprecipitate, solubilised at about neutral pH,
b) subjecting the solution to adsorption with Al(OH)$_3$ and removing the resulting gel,
c) virus inactivating the resulting solution of step b) by a solvent/detergent (S/D) treatment, extraction of S/D reagents with vegetable oil and contacting the water-phase with a TMAE resin,
d) addition of at least one chelating agent to obtain a chelating agent concentration for example of 3 mM to 100 mM in the resulting water phase of step c),
e) precipitation of fibrinogen from the chelating agent containing water phase from step d), by adding glycine until a final concentration of about 1M glycine is reached, and separating of the resulting fibrinogen paste,
f) extraction of fibrinogen from the fibrinogen paste by a 20 mM TRIS buffer at a pH of about 8.0, filtration and,
g) loading the filtered solution of step f) onto an anion exchange resin comprising trimethyl-amino groups grafted to a hydroxylated methacrylic polymer backbone via linking groups and washing off loosely bound substances with a wash buffer of about 12.0 mS/cm conductivity,
h) elution of fibrinogen with an elution buffer containing about 1.5 g/l sodium citrate, about 7.0 g/l sodium chloride and about 10.0 g/l glycine, in particular adjusted to a pH of about 7.0 and a conductivity of 13.1-15 mS/cm,
i) filtering over at least one nanofilter
j) concentrating, formulating, sterile filtering, filling into suitable containers, and optionally lyophilisation.

Subject matter of the present invention is also a fibrinogen enriched fraction obtainable according to the manufacturing process of the invention.

The fibrinogen concentrate is filled into final containers after sterile filtration and it may be stored in liquid, liquid frozen or lyophilised form. Suitable containers are glass vials or bottles or plastic bags eventually comprising a membrane allowing lyophilisation while the bag is tightly sealed off for fluids.

Fibrinogen produced according to this process is characterised by very low amounts of impurities which ascertain the nativity of the product and allows long term treatment of people in need. FXIII is preferable at the concentration contained, because it supports stabilisation of the formed fibrin, while an overload of this transglutaminase is avoided.

The term "comprising", "comprise" or "comprises" can also be replaced by "consisting", "consist" or "consists" without altering the disclosure of the description.

DETAILED DESCRIPTION

Figure 1:
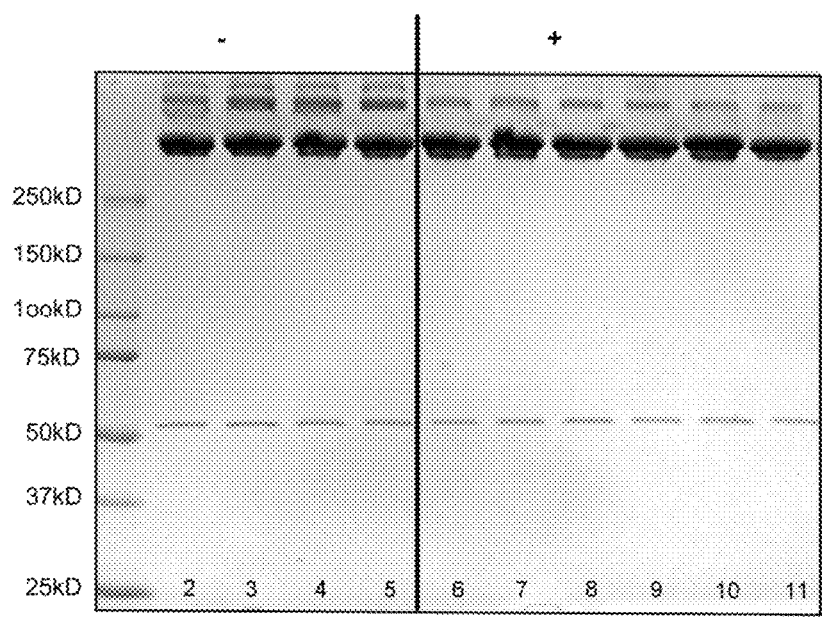
FIG. 1 depicts a SDS-Page at non-reducing conditions of products produced according to the process of the present invention (Lanes 6-11 also indicated as "+") and the product of patent application WO-A1-2012/038410 (Lanes 2-5 also indicated as "−").

Although in principle all fibrinogen containing sources can be used according to the invention, cryoprecipitate is a preferred source and in the following the cryoprecipitate serves as a typical source of fibrinogen in the further description of the manufacturing process of the invention.

Typically cryoprecipitate is reconstituted or solubilised under suitable buffer conditions in particular at about neutral pH (6.9-7.0 for example in a solution buffer containing Na-citrate and NaCl), subjected to adsorption in particular with Al(OH)$_3$ and the resulting gel removed e.g. by centrifugation. The supernatant can then become virus inactivated for example by solvent/detergent (S/D) treatment. This method is well known to the skilled person and has been originally described in EP-A1-131 740. S/D compounds such as Triton (O-[4-(1,1,3,3-Tetramethylbutyl) phenoxy]-polyethoxyethanole) and TnBP (Tri-n-butyl-phosphate) are in particular removed by extraction with castor oil. For further purification the water-phase can be subjected to a chromatographic process. Typically this can be performed by contacting the water-phase with a strong anion-exchange gel, tri-methyl-amino-ethyl (TMAE) grafted on matrix material, such as Fractogel® EMD-TMAE. Good results are achievable if the chromatography is performed with buffers having a pH-value of 6.9-7.1 and an osmolality of 570-610 mosmol/l. Under these conditions fibrinogen is not bound to the stationary phase and hence found in the flow-through or supernatant, the latter if a batch-chromatography process is performed.

Unbound fibrinogen solution, containing typically about 40 g/l (Clauss' turbidometric method) is adjusted to pH=7.0-8.0, in particular to pH=7.3-7.5, with a buffer containing at least one chelating agent. Suitable chelating agents are $Ca^{2+}$-chelating agents in particular 1,2-bis(o-amino)ethane-N,N,N',N'-tetraacetic acid (BAPTA), diethylene-triamine-pentaacetic acid (DTPA), ethylenediamine-tetraacetic acid (EDTA), ethylene-glycol-tetraacetic acid (EGTA) and nitrilo-triacetic acid (NTA) at concentrations of 3 mM to 100 mM, in particular of 5 mM to 50 mM, even more particular of 5 mM to 20 mM. Thereafter a suitable precipitating agent, for example glycine, is added to end up at a concentration of 0.8-1.2 M, in particular 0.9-1.1M the resulting solution can be stirred for 60-120 min to precipitate fibrinogen. Precipitation can be performed in a temperature range of +4.1° C. to +40° C., as long as cryoprecipitation is omitted, in particular in the range of +5° C. to 37° C., more particular from 5.1° C. to 30° C., even more particular at 10°-20° C. The fibrinogen containing precipitate can then be separated by centrifugation and this intermediate fibrinogen paste might be stored at ≤−60° C., preferably at −100° C. to −65° C., for at least 6 months, if the intermediate fibrinogen paste is not processed without delay, but a storage time of 1 day up to 6 months is preferred. Already a single precipitation e.g. with glycine provides a fibrinogen paste sufficiently pure for further processing.

Fibrinogen is then extracted from thus prepared intermediate by a 10-30 mM tris(hydroxymethyl)aminomethane buffer (Tris buffer) free of chelating agent at a pH value from 7.5 to 8.5, in particular a 15-25 mM Tris buffer with pH=7.5-8.5. Extraction takes place for 10-120 minutes, in particular for 15-90 minutes, even more particular for 20-60 minutes during stirring. The suspension obtained can then be filtered off and subjected to ultra/diafiltration for example against 5 times of the suspension volume of the same or a different buffer.

The resulting fibrinogen containing solution is then loaded onto an anion-exchange gel preferably selected from a group of tertiary or quaternary amino groups as ligands grafted to a matrix. Said functional groups are selected from well known diethyl-amino-ethyl (DEAE) or, in the case of a strong anion exchange gel, from groups such as tri-methyl-amino, tri-methyl-amino-ethyl (TMAE) and other groups whereas the carrier material may be composed of cellulose, agarose, silica, polymeric or ceramic material. Good results, in particular in the reduction of fibronectin and vitronectin, can be achieved with trimethyl-amino groups grafted to a hydroxylated methacrylic polymer via a linking group such as GigaCap Q-650M®. This is very surprising as the chemically similar Marco-Prep High Q®, a methacrylic copolymer composed of diethylene-glycol-dimethacrylate/glycidyl-methacrylate also with trimethyl-amino ligands but misses the hydroxyl functionality in its polymeric backbone, is less efficient in the reduction of said two proteins. The effective reduction of the sticky fibronectin is very advantageous for optional filtrations, such as ultra/diafiltration or nanofiltration, as the lifetime of filters is increased due to reduced clogging. If the process is intended to include nanofiltration, it is preferred to perform the process with a diluted solution, in particular with a cascade of nanofilters. The chromatographic gel or resin is in particular preequilibrated with the same buffer as used for resuspending the intermediate fibrinogen paste before applying the fibrinogen solution. Loosely bound substances were washed out with equilibration buffer followed by washing buffer (1.5 g/l sodium citrate, 6.0 g/l sodium chloride, adjusted to pH=6.8-7.2, preferably 6.9-7.1, and possessing the conductivity of 11.0-13.0 mS/cm at room temperature of 20-25° C.).

Fibrinogen can then be eluted from the chromatographic column with an elution buffer containing 1.5 g/l sodium citrate, and 10.0 g/l glycine in particular adjusted to the same pH range as the washing buffer e.g. by HCl and/or NaOH and adjusted with about 7.0 g/l NaCl to the conductivity of 13.1-15 mS/cm at room temperature of 20° C.-25° C. Approximately 74% of the fibrinogen applied onto the column is recovered in the eluate, whilst fibronectin is almost completely removed from the fibrinogen containing eluate. Advantageously a filtration in particular a nanofiltration is performed.

This filtered fibrinogen solution can further be concentrated by ultra/diafiltration to about 20-26 g/l and sterile filtered with membranes of ≤0.2 μm nominal pore size. Persons skilled in the art know that other concentrations, such as 1-19.9 g/l or 26.01-30 g/l or even higher are also achievable. The fibrinogen concentrate of the present invention may also be formulated with additives like stabilisers known by the skilled person such as carbohydrates, e.g. sucrose, trehalose, amino acids, e.g. glycine, histidine, alanine, arginine and detergents, e.g. polyoxyethylene-(20)-sorbitan-monooleate (TWEEN 80®). This sterile filtered bulk is stored at −60° C. or lower, in particular at −65° C. to −80° C., before being sterile filtered for a second time and filled into final containers and optionally freeze dried or directly filled into final containers and optionally freeze dried without a second sterile filtration.

It is not necessary to add further buffers, stabilisers, protease inhibitors, like AT-III, heparin-cofactor-II and C1-esterase-inhibitor, or other compounds, like coagulation factor XIII (F XIII). Coagulation factor XIII is present in the concentrate with activities of ≥0.05 IU per mg fibrinogen (Clauss method), in particular with activities of 0.05-0.30 IU/mg. The fibrinogen concentrate of the present invention is further characterised by a low content of compounds of higher molecular weight than fibrinogen (HMW), determined as % of total area by size exclusion chromatography at 280 nm. The fibrinogen concentrate of the present invention contains less than 11% HMW, in particular 2-10% when the concentration of the chelating agent was at least 3 mmol/l. The use of chelating agents at concentrations of at least 5 mmol/l reduced the HMW-content to 2-6%. Some albumin may also be present in a concentration of about 16 ng per mg fibrinogen. Antithrombin-III (AT-III) and proteolytic activity were not detectible, i.e. an AT-III concentration of less than 0.2 IU/ml and a proteolytic activity of less than 2 U per liter (<2 U/l), which equates to less than 0.01 IU AT-III per mg fibrinogen and less than 0.1 mU proteolytic activity per mg fibrinogen, when being measured in a solution of the final product containing fibrinogen in a concentration of 20 mg/ml. The invention is further explained by the following non-limiting examples.

EXAMPLE I

Cryoprecipitate, produced from plasma by established methods, was reconstituted or solubilised at about neutral pH, subjected to adsorption with $Al(OH)_3$ and the resulting gel removed by centrifugation. The supernatant was then virus inactivated by solvent/detergent (S/D) treatment. S/D compounds, according to EP-A1-0 131 740 were extracted with vegetable oil and the water-phase was contacted with Fractogel® EMD-TMAE. Chromatographic conditions (pH-value of 6.9-7.1 and an osmolality of 570-610 mosmol/l) were employed under which the fibrinogen did not bind to the gel and hence was found in the flow-through or supernatant.

The solution of unbound fibrinogen was admixed with EDTA until the EDTA concentration reached 10 mM and the EDTA containing fibrinogen solution was stirred at about 15° C. for about 60 minutes after addition of glycine (1 mol/l final concentration and pH=7.4) to precipitate fibrinogen. The fibrinogen containing precipitate was then separated by centrifugation, yielding an intermediate fibrinogen paste.

The fibrinogen was extracted by stirring for about 30 minutes from thus prepared intermediate by a 20 mM Tris buffer (pH=about 8.0) lacking a chelating agent and the suspension obtained was then filtered and subjected to ultra/diafiltration.

The resulting fibrinogen containing solution was then loaded onto GigaCap Q-650M® and the chromatographic gel or resin was preequilibrated with the same Tris buffer as used for resuspension before applying the fibrinogen solution. Loosely bound substances were washed out with the equilibration buffer followed by washing with a wash buffer (1.5 g/l sodium citrate, 6.0 g/l sodium chloride, adjusted to about pH 7.0 and a conductivity of about 12.0 mS/cm). Fibrinogen was then eluted from the chromatographic column with an elution buffer (1.5 g/l sodium citrate, and 10.0 g/l glycine adjusted to the same pH as the washing buffer and adjusted with about 7.0 g/l NaCl to the conductivity of 13.1-15 mS/cm). Nanofiltration was performed by successive passage of fibrinogen solution over nanofilters of decreasing pore size from 75 nm down to <35 nm.

The resulting fibrinogen solution was concentrated, formulated and sterile filtered. This sterile filtered bulk was stored for 5 days at −80° C. before being sterile filtered for a second time and filled into final containers. One part of final containers was lyophilised while the other part was kept as a liquid formulation. No detectable amounts of chelating agents were observed in the lyophilised product or the liquid concentrate.

Reconstitution of lyophilisates was accomplished by addition of water for injection (WFI) up to the concentration before lyophilisation.

Examples II-XII were performed in the same way as example I but comprised variation of type and concentration of chelating agents as well as variations of extraction time. While parameters like protein content, fibrinogen-antigen content or fibrinopeptide-A content were not significantly influenced by these variations when being normalised to 1 mg fibrinogen, it was observed that the content of compounds of higher molecular weight than fibrinogen (HMW), determined by size exclusion chromatography, exceeded 10% when the concentration of the complexing agent was less than 3 mmol/l. Example XIII was prepared according to the process of WO-A1-2012/038410, i.e. without any chelating agent present during purification. The outcome of these variations is summarised in table 1.

TABLE 1

| Example | Substance | mmol/l | HMW % |
|---------|-----------|--------|-------|
| II | EDTA | 1 | 18 |
| III | EDTA | 3 | 10 |
| IV | EDTA | 5 | 4 |

TABLE 1-continued

| Example | Substance | mmol/l | HMW % |
|---------|-----------|--------|-------|
| V | EDTA | 20 | 4 |
| VI | EDTA | 50 | 4 |
| XIII | — | 0 | 20 |
| XI | EGTA | 1 | 13 |
| XII | BAPTA | 1 | 22 |
| IX | EGTA | 5 | 3 |
| X | BAPTA | 5 | 6 |
| I | EDTA | 10 | 3 |
| VII | EGTA | 10 | 2 |
| VIII | BAPTA | 10 | 4 |

A set of experiments was performed to determine a suitable extraction time range as a compromise between yield and purity of the extracted fibrinogen intermediate. The suitable extraction time range was determined to be between 10 to 120 minutes as less extraction time provided a very pure intermediate at the cost of fibrinogen yield, while at extraction times exceeding 120 minutes it was observed that some impurities began to redissolve without a significant gain in fibrinogen yield.

Comparison with WO-A1-2012/038410.

A difference between the present invention and WO-A1-2012/038410 is represented by the addition of a chelating agent prior to precipitation of fibrinogen by a suitable precipitation agent, like glycine, and replacement of the following resuspension step in WO-A1-2012/038410 by an extraction. Said modification resulted in an unexpected increase of coagulation factor XIII activity in the final product of the present invention, i.e. up to 0.30 IU/mg fibrinogen (fibrinogen concentration 20-25 mg/ml; determined by the Clauss method), as well as an increased yield.

FIG. 1 depicts a SDS-Page at non-reducing conditions revealing less high molecular weight compounds in typical products produced according to the process of the present invention (Lanes 6-11 also indicated as "+") compared to the product of patent application WO-A1-2012/038410 (Lanes 2-5 also indicated as "−"). The protein band closest to 250 kD represents fibrinogen while those above the fibrinogen band are compounds of higher molecular weight. The protein band at about 50 kD represents albumin. Lane 1 displays the molecular weight markers.

Figure 2:
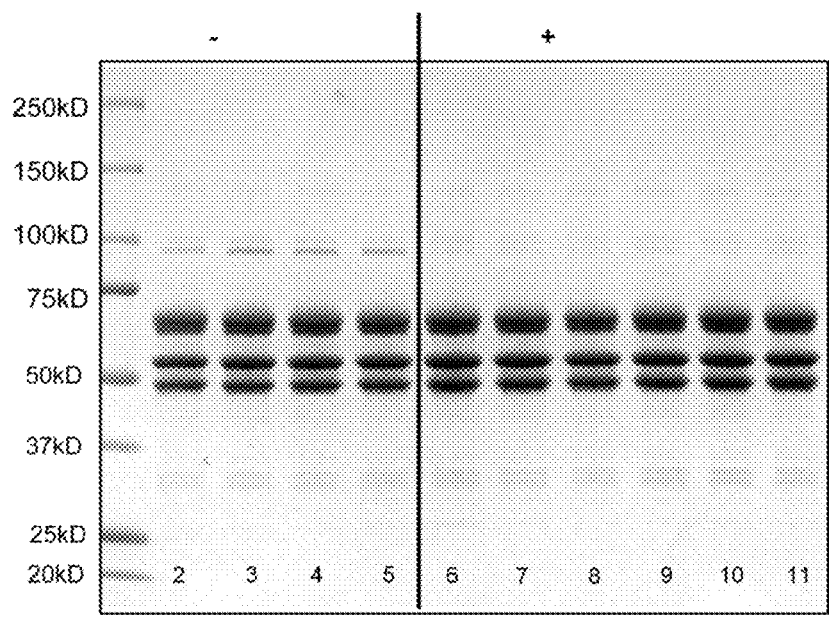
FIG. 2 depicts a SDS-Page at reducing conditions of products produced according to the process of the present invention (Lanes 6-11 also indicated as "+") and the product of patent application WO-A1-2012/038410 (Lanes 2-5 also indicated as "−").

FIG. 2 depicts a SDS-Page at reducing conditions. Tested products are the same as in FIG. 1 and in the same order and they are consequently indicated in the same manner as in FIG. 1, i.e. "+" for products prepared by a process according to the present invention, while "−" indicates products prepared by a process according to WO-A1-2012/038410. The major bands at about 50-70 kD represent the α-, β- and γ-chains of fibrinogen. The protein band at about 100 kD represent the dimer of the fibrinogen γ-chain. The faint band at about 30 kD is caused by fibrinogen fragments. Lane 1 displays the molecular weight markers.

Comparison with WO-A2-2009/155626

Differences between the products of the present invention and those of WO-A2-2009/155626 were investigated by analysis of products prepared by the processes of WO-A2-2009/155626, in particular by combination of disclosed examples 1 and 6, which results in a nanofiltered and lyophilised product. It was observed that the product of WO-A2-2009/155626 contained 1% of compounds of higher molecular weight than fibrinogen, determined by size exclusion chromatography, and a coagulation factor XIII activity of about 0.41 IU/mg fibrinogen.

The invention claimed is:

1. A pharmaceutical fibrinogen solution product comprising

2% to 6% of compounds of higher molecular weight than fibrinogen, with fibrinogen having an apparent molecular weight of 340 kD, determined as % of total area by size exclusion chromatography at 280 nm;

a coagulation factor XIII activity in concentrations of 0.05-0.30 IU/mg fibrinogen; and having no detectable amount of antithrombin-III (AT-III) and no detectable amount of proteolytic activity as measured by an AT-III concentration of less than 0.2 IU/ml and a proteolytic activity of less than 2 U per litre (<2 U/l), which equates to less than 0.01 IU AT-III per mg fibrinogen and less than 0.1 mU proteolytic activity per mg fibrinogen as measured in a solution of the product containing fibrinogen in a concentration of 20 mg/mL;

wherein said fibrinogen solution product is obtained by a process comprising precipitation of fibrinogen by a precipitating agent from a fibrinogen containing solution in the presence of one or more chelating agent(s) to form a fibrinogen paste and removal of the supernatant from the fibrinogen paste, characterised in that fibrinogen is extracted from the paste forming a liquid fraction containing fibrinogen, and an undissolved residue, which is separated from the liquid, without addition of one or more protease inhibitor(s).

2. The pharmaceutical fibrinogen solution product according to claim 1, wherein the process comprises precipitating the fibrinogen with the precipitating agent from the fibrinogen containing source in the presence of the one or more chelating agent(s) to form the fibrinogen paste, removing the supernatant from the fibrinogen paste, extracting the fibrinogen from the fibrinogen paste in an aqueous medium void of the chelating agent(s) for a suitable extraction time thereby forming the liquid fraction containing fibrinogen and the undissolved residue, and separating the undissolved residue from the liquid fraction containing fibrinogen, wherein addition of one or more protease inhibitor(s) is omitted in all steps of the process, wherein the fibrinogen is precipitated in a temperature range of from 4.1° C. to 40° C., and the one or more protease inhibitor(s) is selected from the group consisting of C1-protease inhibitors, trypsin inhibitors, thrombin inhibitors, antithrombin-III (AT-III), heparin-cofactor-II, aprotinin, pepstatin, leupeptin and epsilon-aminocaproic acid.

3. The pharmaceutical fibrinogen solution product according to claim 1, wherein the concentration of the chelating agent in the water phase is 3 mM to 100 mM.

4. The pharmaceutical fibrinogen solution product according to claim 1, wherein the process further comprises the steps of:

a) solubilising a cryoprecipitate, solubilised at about neutral pH to form the solution;

b) subjecting the solution to adsorption with Al(OH)$_3$ and removing a resulting gel;

c) virus inactivating the resulting solution of step b) by a solvent/detergent (S/D) treatment, extraction of S/D reagents with vegetable oil and contacting a water-phase with a TMAE resin at a pH-value of 6.9-7.1 and an osmolality of 570-610 mosmol/l;

d) adding at least one chelating agent to the resulting water phase of step c), wherein a concentration of the chelating agent in the water phase is 3 mM to 100 mM;

e) precipitating the fibrinogen from the chelating agent-containing water phase from step d) by adding glycine until a final concentration of about 1M glycine is reached to form the fibrinogen paste, and separating the resulting fibrinogen paste;

f) extracting the fibrinogen from the fibrinogen paste by a 20 mM TRIS buffer at a pH of about 8.0 and filtering to form a filtered solution;

g) loading the filtered solution of step f) onto an anion exchange resin comprising trimethyl-amino groups grafted to a hydroxylated methacrylic polymer backbone via linking groups and washing off loosely bound substances with a wash buffer of about 12.0 mS/cm conductivity;

h) eluting the fibrinogen with an elution buffer containing about 1.5 g/l sodium citrate, about 7.0 g/l sodium chloride, and about 10.0 g/l glycine, the elution buffer adjusted to a pH of about 7.0 and a conductivity of 13.1-15 mS/cm;

i) filtering the fibrinogen over at least one nanofilter; and j) concentrating, formulating, sterile filtering, filling into suitable containers, and optionally lyophilising the fibrinogen;

wherein addition of one or more protease inhibitor(s) is omitted, and the fibrinogen product having less than 2%-6% of compounds of higher molecular weight than fibrinogen, determined as % of total area by size exclusion chromatography at 280 nm.

5. A pharmaceutical fibrinogen solution product obtained by a process comprising lyophilizing the fibrinogen solution product of claim 1.

6. The pharmaceutical fibrinogen solution product according to claim 4, wherein the anion exchange resin comprises a support material comprising a hydroxylated polymer backbone with grafted tertiary or quaternary amino groups.

7. The pharmaceutical fibrinogen solution product of claim 5, which, when reconstituted with water to a concentration of 20 mg/mL, comprises:

2% to 6% of compounds of higher molecular weight than fibrinogen, determined as % of total area by size exclusion chromatography at 280 nm;

a coagulation factor XIII activity in concentrations of 0.05-0.30 IU/mg fibrinogen; and has no detectable amount of antithrombin-III (AT-III) and no detectable amount of proteolytic activity as measured by an AT-III concentration of less than 0.2 IU/mL and a proteolytic activity of less than 2 U per litre (<2 U/l), which equates to less than 0.01 IU AT-III per mg fibrinogen and less than 0.1 mU proteolytic activity per mg fibrinogen.

* * * * *